United States Patent [19]

Marsoner

[11] Patent Number: 4,529,495
[45] Date of Patent: Jul. 16, 1985

[54] MEASURING SET-UP WITH AT LEAST ONE SENSOR

[75] Inventor: Hermann Marsoner, Steinberg, Austria

[73] Assignee: AVL AG, Schaffhausen, Switzerland

[21] Appl. No.: 577,835

[22] Filed: Feb. 7, 1984

[30] Foreign Application Priority Data

Feb. 9, 1983 [AT] Austria .................................. 447/83

[51] Int. Cl.³ ............................................. G01N 27/28
[52] U.S. Cl. .................................... 204/411; 204/415; 356/246; 422/68; 422/102
[58] Field of Search ............... 204/415, 416, 418, 419, 204/420, 403, 412, 411, 1 P; 422/102, 68; 356/246, 440

[56] References Cited

U.S. PATENT DOCUMENTS

| | | | |
|---|---|---|---|
| 3,380,905 | 4/1968 | Clark | 204/415 |
| 3,855,100 | 12/1974 | Haddad | 204/420 |
| 3,997,420 | 12/1976 | Buzza | 204/415 X |
| 4,230,537 | 10/1980 | Delente | 204/1 T |
| 4,311,151 | 1/1982 | Hagihara | 128/635 |
| 4,401,547 | 8/1983 | Schinkmann et al. | 204/415 |
| 4,444,646 | 4/1984 | Metzger et al. | 204/415 |

Primary Examiner—G. L. Kaplan
Attorney, Agent, or Firm—Watson, Cole, Grindle & Watson

[57] ABSTRACT

Between a substance to be analyzed and a sensor there is placed at least one membrane, forming part of a sample vessel containing a sample to be analyzed and being permeable for a species depending on the substance to be analyzed. This membrane constitutes at least one wall of the sample vessel, through which the active sensor surface may be brought into contact with the substance to be analyzed. The sensor is designed as a separate unit which is movable relative to the sample vessel, with which its membrane may be brought into contact. For the purpose of measurement the sensor is contacted by the membrane stretching over the active sensor surface which in itself does not carry a membrane.

In this way the sensor cannot be contaminated by the sample, and the device may be successfully used for series measurements.

7 Claims, 7 Drawing Figures

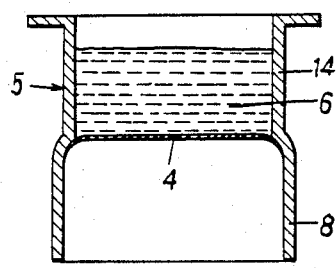
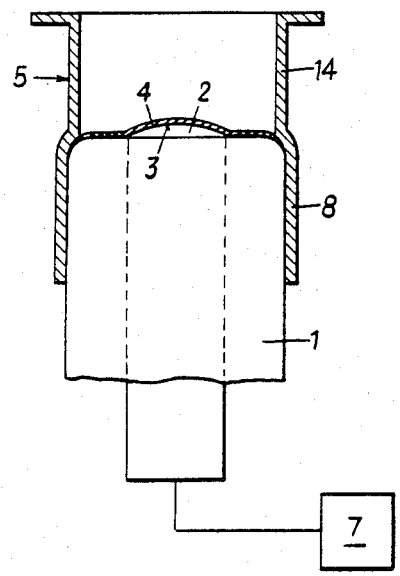
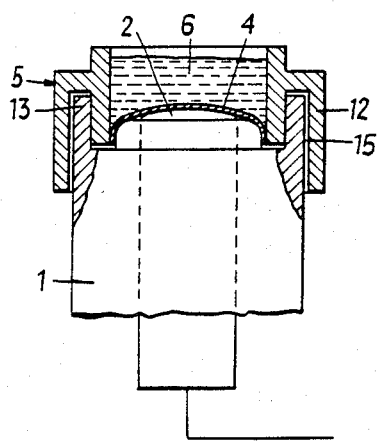
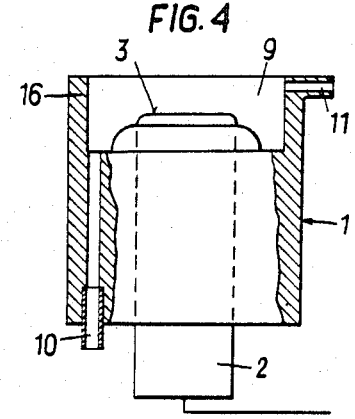
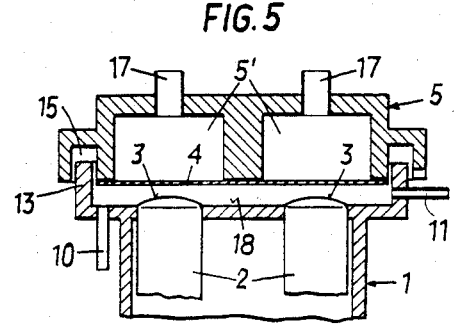
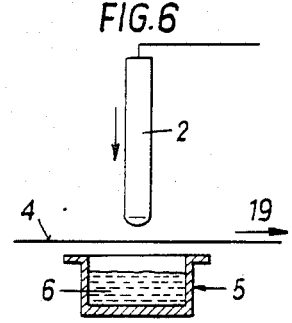
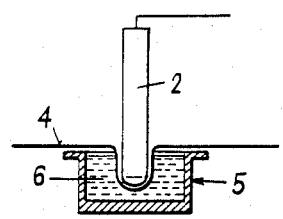

MEASURING SET-UP WITH AT LEAST ONE SENSOR

BACKGROUND OF THE INVENTION

This invention relates to a measuring set-up, especially for determining the concentration of substances that are preferably contained in sample vessels, e.g., biological liquids, comprising at least one electrochemical, optical, calorimetric, ion-selective, or similar such sensor, with at least one thin membrane being placed between the substance to be analyzed and the sensor, or rather the active surface of the sensor. The membrane forms part of the sample vessel and is permeable for a species or measurement variable (such as the ionic concentration) depending on the particular substance and its properties, especially its concentration, and through which membrane the active sensor surface may be brought into contact with the substance, and which membrane will cover or enclose the substance to be analyzed and will constitute at least one wall of the sample vessel containing this substance, the active sensor surface itself not carrying a membrane.

DESCRIPTION OF THE PRIOR ART

Set-ups with ion-sensitive electrochemical sensors for measuring ionic concentrations in liquids, above all biological liquids, are known. Besides, there are devices for performing such analyses automatically, in which the samples are usually sucked into analyzing compartments where they are brought into contact with the sensors. In set-ups of this kind a number of means must be provided for the cleaning of the analyzing compartment and for feeding it with standard solutions used to calibrate the sensors. Such automatic analyzing devices are of great technical complexity and, as a consequence, are rather costly.

Less complex devices for analyzing electrolytic concentrations with the use of ion-sensitive electrochemical sensors have also been described which function in a simpler manner, e.g., by jointly dipping a number of rod-shaped sensors into a vessel containing the sample liquid. At the end of the measuring process the rod-shaped sensors are rinsed with a washing liquid, any remains of which will have to be carefully removed. Handling the sample in this way may involve unpleasant contacts and may lead to incorrect test results if the rinsing and preparatory steps have not been performed with the utmost care. All known systems are characterized by frequent contaminations of the sensors due to the direct contact between the active measuring surfaces of the sensors and the biological sample liquids.

In addition, there is known, e.g., from British Patent Specification 1,080,343, an integrated unit with the sample vessel and the sensor being configured in one single piece. In this case the sample vessel has the shape of a beaker with a membrane inside for receiving the sample. The sensor and the vessel are rigidly connected; for the purpose of analysis the test sample or liquid is filled into the membrane thus covering the sensor. With this kind of arrangement it is essential that a drop of an electrolytic solution be placed between the membrane and the sensor, which ensures proper functioning of the sensor by establishing a bridge between the membrane and the sensor surface. After the sample has been filled into the membrane, the membrane bag containing the sample will be pressed against the sensor surface due to the weight of the sample, without stretching and without covering the sensor under stress. The membrane bag containing the sample must be supported by a separate vessel, i.e., the above beaker, as it has no mechanical stability and could otherwise not be placed upon the sensors. This type of measuring device which requires expensive cleaning after each use, is not suitable for performing series measurements economically. Furthermore, there is no well-defined contact between the sensors and the sample.

SUMMARY OF THE INVENTION

In a measuring set-up according to the present invention the disadvantages of the known systems are eliminated mainly by configuring the sensor as a separate unit which is independent of and movable relative to the sample vessel with whose membrane it may be brought into contact, and by designing the membrane such that it may be deformed by the sensor, or rather the active sensor surface, and that it will stretch tightly over the active sensor surface, offering a perfect seal during measurement of the sample substances. By separating the sensor from the membrane containing the sample, and by enabling a well-defined contact between the sensor and the sample vessel, the sensor will be ready for immediate re-use, any contamination having been avoided. Because of this well-defined contact between the membrane and the sensor, reproducible measurement results are achieved and handling of the equipment is simplified. For instance, if the bottom of the sample vessel consists of a thin, permeable membrane which is attached to the other walls of the vessel in a leak-proof way, the sample vessel may be placed upon the sensitive tips or active surfaces of the sensors such that they are tightly and smoothly covered by the thin permeable membrane. In this way a direct connection with the active sensor surfaces is established for the species to be measured in the sample, or the sample liquid, without involving any direct contact between the sample and the sensors.

In a set-up designed according to the invention the concentration of various ions may be measured in this manner. After measurement the sample vessel is removed and may be discarded together with the sample. Since no direct contact has taken place between the sample and the sensors, the sensors remain ready for use. Thus another sample in another sample vessel may be placed upon the sensors immediately afterwards, and a new measuring cycle may commence.

According to a further embodiment of the present invention provisions are made for a membrane stretching over an opening in the sample vessel, preferably at a distance from the substance to be analyzed or the sample vessel, which may be deformed and brought into contact with the substance, or pushed into the substance by a pressure of the sensor.

The present set-up is not restricted to the use of ion-sensitive electrochemical sensors. By the term sensors those specific sensors of a known type are to be understood for which sufficient permeation through a thin membrane of the sample vessel may be ensured. For example, oxygen, carbon dioxide, ammonia, glucose, lactate, urea, creatinine could be measured by means of direct specific sensors. Optical sensors, e.g., fluorescence-optical sensors, or calorimetric sensors may also be employed. Furthermore, this set-up is not limited to the analysis of biological liquids, but may be used in conjunction with any known variant of specific sensors, for determining the most diverse sample properties, above all sample concentrations.

All sample properties suitable for analysis by means of sensors via permeable membranes, may be measured without any direct contact between the sensors and the sample substance. The membrane need not have any selective permeability since selectivity is ensured by the sensors themselves. However, selectivity of the sensors may be supported by the use of a perm-selective membrane.

In a further embodiment of the invention, which is preferred in practice for rapid measurements, a number of sensors are combined in one sensor housing in which the active sensor surfaces are located side by side in one plane, and at a mutual distance from one another which corresponds to the distance between the measuring compartments in the sample vessel, or the distance between several sample vessels combined into one unit. Moreover, a further embodiment provides that the lower part of a sample vessel whose bottom is formed by a membrane, be placed from above onto a sensor or sensor housing, or rather the active surface of this sensor, the latter being inserted into the sample vessel by pressing against the membrane, deforming it and thus establishing measuring contact with the substance to be analysed.

The sensor housing provides a supporting frame in which the sensors may be integrated, this frame presenting a plane in which are situated the sensitive or active surfaces of the sensors. These sensitive surfaces may be located, e.g., level with the supporting frame such that a smooth plane is formed, or the sensitive surfaces may slightly protrude from the plane of the supporting frame. The appropriate sample vessels are designed such that one of their boundary surfaces, preferably the bottom, consists of a thin, flexible, ion-permeable and-/or gas-permeable membrane which can be stretched over the active sensor surface.

Mutual positioning may be facilitated by providing the sensor housing and/or the sample vessel with stops, guidings, projections and recesses, grooves and ridges, which may mutually engage.

In a further embodiment of the invention an enclosed space is provided around at least one active sensor surface on the surface of the sensor housing, into which a calibrating or standard solution may be filled or in which it may be circulated, which solution will cover the active sensor surface. In this case it will be of advantage if inlet and outlet channels are provided for the calibrating or standard solution, and if the level of the solution may be controlled by an overflow channel. It is essential that the active sensor surfaces be fully covered-for this a thin liquid layer may suffice. A standard solution could be used for this purpose. As standard solutions may be produced with a high degree of purity, and as their components are fully known, direct contact between the standard solutions and the sensors is harmless, or less harmful for the active sensor surfaces than direct contact with the sample material or substance. With this type of arrangement, the sensors could be calibrated by feeding the standard solution directly into the compartment above the surface carrying the sensors, on which the sample vessels with their thin permeable membranes may be placed with a tight fit. Positioning of the sample vessels will displace the reference solution contained in this compartment except for a very thin boundary layer only. Thus contact between the active sensor surfaces and the sample material may be guaranteed. The overflow channel or another suitable device ensures that a certain liquid level of the desired standard solution is automatically re-established above the active sensor surfaces as soon as the sample vessel has been removed after measurement, permitting the sensors to be calibrated again. Calibration may also be achieved by providing sample vessels filled with standard solutions, which may be placed on the sensors, or rather the active sensor surfaces, following which the sensors are calibrated by conventional methods.

According to a further embodiment of the invention, the sensor housing, the sample vessel and the compartment containing the standard solution are designed such that the sample vessel may be positioned in a simple and safe manner.

It is possible to combine several sample vessels into one common unit which may be placed upon a sensor housing, preferably such that each sample vessel is assigned a sensor of its own.

It should be pointed out that it may be sensible to have the sample vessels stationary, i.e., to use them as the basis of the set-up, while the sensors are brought into contact from above or sideways with the membrane-covered surfaces of the sample vessels.

It is possible to place the sample vessel in a supporting frame permitting an exact positioning of the sample vessel on the sensor housing; this supporting frame will also be used for removing the sample vessel after the measurement has been completed, e.g., by lifting it automatically. This is of advantage in series measurements.

DESCRIPTION OF THE DRAWING

Following is a more detailed description of the present invention, as illustrated by the enclosed drawing, in which FIG. 1 exhibits a sample vessel, FIGS. 2 and 3 show a sample vessel placed upon a sensor, FIG. 4 presents a variant of a sample vessel embodying the invention, FIG. 5 presents a sample vessel housing, respective a sample vessel with several measuring compartments, which is placed upon a sensor housing, and FIGS. 6 and 7 each show a variant of the set-up proposed by the present invention.

DESCRIPTION OF THE PREFERRED EMBODIMENTS

FIG. 1 shows a sample vessel 5 which may be open or closed at the top or which may be provided with a sample feed opening. The upper part 14 of the cylindrical sample vessel 5 which is open in this case, is separated from the lower part 8 which is also cylindrical, by a thin permeable membrane 4. In the upper part 14 is contained the substance 6 to be analyzed, i.e., the sample-a liquid sample in this case.

As is shown in FIG. 2, a sensor 2 located in a sensor housing 1 may be inserted into the lower part 8 of the sample vessel 5, or rather, the sample vessel 5 may be placed upon the sensor housing 1. The active sensor surface 3 is covered by the tightly stretched membrane 4, and the measurement is performed through the membrane 4, for which purpose the sensor 2 is connected to an evaluation unit 7. The sensor housing 1 and the lower part 8 of the sample vessel 5 are shaped to match each other; the shapes themselves may vary, e.g., they may have square, round, rectangular or quadrangular cross-sections.

If the sample carrier 5 is closed at the top, it may be turned upside down and the sensor 2 may be inserted into the sample vessel 5 from above.

It would also be possible to use a side-wall, e.g., of a cubical vessel or a vessel in the shape of a rectangular block, for housing a sensor, in which case the respective side-wall would be formed by a permeable membrane 4.

FIG. 3 presents a set-up in which the sample vessel 5 is provided with grooves 15 with adjacent lugs 12, which grooves may engage ridges 13 of the sensor housing 1. If the sample vessel 5 is closed, this device-like all others-may be turned upside down.

As can be seen from FIGS. 1 to 3, a sample may be easily exchanged after measurement, the sensor surface 3 need not be cleaned and a new sample vessel 5 may be placed upon the sensor as soon as the previous vessel has been removed.

FIG. 4 shows a sensor housing 1 with a feed channel 10 for a liquid covering the active sensor surface 3, preferably a calibrating or standard solution.

The side-walls 16 prevent the liquid from flowing off, while its level is maintained constant by an overflow or outlet channel 11. If a sample vessel 5 is placed on the sensor housing 1, the liquid between the membrane and the sensor surface 3 is displaced and the measuring process is performed via the elastic membrane stretching over the sensor surface 3. If inelastic membranes are used, they may be inserted without being tightened; in this case they are kept in contact with the sensor surface by the pressure of the sample liquid.

FIG. 5 shows a multiple sensor housing 1, containing two sensors 2 in this variant. The active sensor surfaces 3 protrude beyond the top surface 18 of the sensor housing 1; they are covered by a liquid flowing in through the feed channel 10 and draining via the outlet channel 11. Lugs and ridges 13 of the sensor housing 1 engage with grooves 15 of the sample vessel 5 which is divided into several measuring compartments 5' closed below by a membrane 4. The measuring compartments may be filled with the sample substances via inlet openings 17, above all, if the sample vessels 5 are of a re-usable kind. In this manner a number of samples may be analysed simultaneously by a number of sensors 2.

There is also the possibility of combining several sample vessels into one vessel housing, in which case the unit resembles that presented in FIG. 5, the individual sample vessels corresponding to the measuring compartments 5'.

FIGS. 6 and 7 present a variant of the set-up described by the present invention. At a distance above an open sample vessel 5 filled with a sample substance 6, or directly on top of the sample vessel 5 a permeable membrane 4 is placed which may be transported in the direction of the arrow 19 and thereby be removed from the sample vessel 5. During the measuring process a sensor 2 located above the membrane 4 is lowered, deforming the membrane 4 or being enveloped by it; in its lowest position (FIG. 7) it is in measuring contact with the liquid 6 via the membrane 4. After the measuring process, the sensor 2 is lifted and the membrane 4 is moved on until a clean part of the membrane 4 lies beneath the sensor 2, or a new membrane 4 is inserted and the sample vessel 5 or the liquid 6 or substance to be analyzed are exchanged. This type of set-up will also permit the use of several sensors 2 in one common housing which may be placed upon sample vessels 5 combined into a housing, the membrane being removable or exchangeable after each measurement. Again, the sensor 2 and the sample vessel 5 may be inserted into a supporting frame which permits a mutual relative movement and is additionally provided with a transport device for the membrane 4.

The sensor housing 1 may also assume the shape of a rectangular block in which the sensors are built in permanently, e.g., pressed in, or in which they are fastened mechanically, e.g., by screwing or plugging. If the block, or the sample vessel 5, has a quadrangular mounting surface or contact opening for the sensor 2 or the sensor housing 1, the sensor 2, or the sensor housing 1, is shaped to match such that mutual inserting or mounting of the components, or a contact between the active sensor surface 2 and the sample substance 6 via the membrane 4 is geometrically determined.

The set-up described by the present invention will also permit flow measurements. In this case the liquid to be analysed is passed through a sample vessel or a channel, etc., into which a sensor may be dipped. A membrane placed above the sample vessel or the channel will prevent any direct contact between sensor and liquid, which membrane is replaced by a new one after each measuring cycle.

I claim:

1. An analyzing apparatus for measuring the properties of a liquid sample, said apparatus including a sample vessel; said sample vessel defining a chamber for containing the liquid sample to be analyzed, one wall of said chamber being composed of a semipermeable membrane, and a separate sensor device; said sensor device including
a support frame formed by a main body portion and a ridge portion extending away from said main body portion and having a free end remote from said main body portion, said main body portion defining an inlet channel therethrough for supplying a calibrating or standardized solution to the interior of said ridge portion, and said ridge portion defining an outlet channel therethrough for discharge of said calibrating or standardized solution from the interior of said ridge portion, and an elongated sensor element; said elongated sensor element having a membrane-free active sensor surface at one end thereof, said sensor element being supported by said main body portion of said support frame such that the end thereof having the active sensor surface extends beyond said main body portion and interiorly of said ridge portion, the active sensor surface of said sensor element being located closer to said main body portion than the free end of said ridge portion such that calibrating or standardized solution supplied to the interior of said ridge portion can cover the active sensor surface of said said sensor element, said sample vessel and said sensor device being engageable such that the wall of the chamber of said sample vessel which is formed by said semi-permeable membrane can be positioned within the ridge portion of said sensor device to enable the semi-permeable membrane to tightly and sealingly stretch over the active sensor surface of said sensor element for the purpose of taking measurements of the properties of the liquid sample in said chamber through said semi-permeable membrane yet avoid direct contact with the liquid sample.

2. The analyzing apparatus as defined in claim 1, wherein said sample vessel includes L-shaped lugs which extend from the sides thereof adjacent to the wall formed of said semipermeable membrane, said L-shaped lugs providing grooves into which the ridge portion of said sensor device are positionable.

3. The analyzing apparatus as defined in claim 1, wherein said sensor device includes a plurality of sensor elements supported by said main body portion, and wherein said sample vessel includes a corresponding plurality of liquid sample-containing chambers, each said liquid sample-containing chambers having a wall formed of a semi-permeable membrane.

4. The analyzing apparatus as defined in claim 1, wherein said sample vessel comprises a generally cylindrical tube hving an upper part with a first diameter and a lower part with a second diameter, said second diameter being larger than said first diameter, and wherein said semi-permeable membrane is located within said generally cylindrical tube between said upper and lower parts, the semi-permeable membrane forming the floor of a liquid sample-containing chamber defined within the upper part of said generally cylindrical tube.

5. The analyzing apparatus as defined in claim 4, wherein the end of the upper part of said generally cylindrical tube opposite said semi-permeable membrane is open.

6. The analyzing apparatus as defined in claim 1, wherein said sample vessel includes channel means for supplying a liquid sample to be analyzed to said chamber.

7. The analyzing apparatus as defined in claim 1, wherein the active sensor surface of said sensor element is convex.

* * * * *